United States Patent [19]

Bolland et al.

[11] Patent Number: 5,280,024

[45] Date of Patent: Jan. 18, 1994

[54] MEDICINAL USE OF 3′,5′-DI-TERT.-BUTYL-4′-HYDROXY FLAVONES

[75] Inventors: Yves Bolland, Vanves; Guy Lewin, Rueil Malmaison; Jean-Paul Vilaine, Chatenay Malabry; Lenaers Albert, Triel sur Seine; Catherine Thollon, Paris, all of France

[73] Assignee: Adir et Compagnie, Courbevoie, France

[21] Appl. No.: 36,814

[22] Filed: Mar. 25, 1993

[30] Foreign Application Priority Data

Mar. 31, 1992 [FR] France .................. 92 03861

[51] Int. Cl.⁵ .................. A61K 31/35; A61K 31/445; A61K 31/535
[52] U.S. Cl. .................. 514/233.5; 514/253; 514/314; 514/320; 514/456; 544/151; 544/376; 546/174; 546/196; 549/403
[58] Field of Search .............. 544/131, 376; 546/174, 546/196; 549/403; 514/233.5, 253, 314, 320, 456

[56] References Cited

U.S. PATENT DOCUMENTS 3,816,466  6/1974  Strandtmann et al. ............ 549/403

Primary Examiner—Robert W. Ramsuer
Attorney, Agent, or Firm—Gordon W. Hueschen

[57] ABSTRACT

Compounds of the general formula (I):

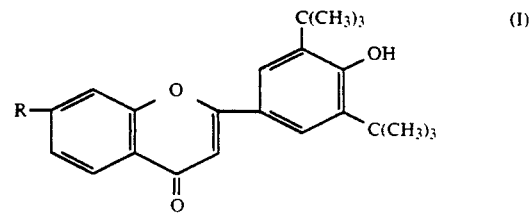

in which R represents:
a hydrogen atom, or
a radical —OR′
in which R′ is as defined in the description.

21 Claims, No Drawings

MEDICINAL USE OF 3',5'-DI-TERT.-BUTYL-4'-HYDROXY FLAVONES

The present invention relates to 3',5'-di-tert.-butyl-4'-hydroxy flavones, a process for the preparation thereof and pharmaceutical compositions containing them.

It relates especially to 3',5'-di-tert.-butyl-4'-hydroxy flavones of the general formula (I):

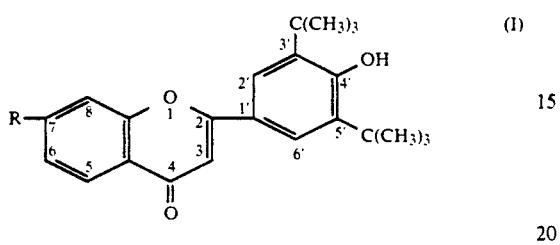

in which

R represents:
hydrogen or
a radical OR' in which R' represents:
  a) hydrogen
  b) an alkyl radical containing from 1 to 10 carbon atoms in a straight or branched chain optionally substituted by one or more substituents selected from the group consisting of:
    α) phenyl and monocyclic or bicyclic aromatic heterocyclic radicals, all optionally substituted by one or more substituents selected from halogen atoms, such as chlorine, bromine or fluorine, and trifluoromethyl and hydroxy radicals and alkyl and alkoxy radicals each having from 1 to 5 carbon atoms in a straight or branched chain,
    β) carboxy,
    γ) alkoxycarbonyl in which the alkoxy group contains from 1 to 5 carbon atoms in a straight or branched chain,
    δ) aminocarbonyl of the formula:

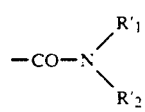

in which each of R'$_1$ and R'$_2$, which may be identical or different, represent: a hydrogen atom, or an alkyl radical having from 1 to 5 carbon atoms in a straight or branched chain, or R'$_1$ and R'$_2$ form together with the nitrogen atom to which they are bonded a heterocyclic radical optionally containing a second hetero atom selected from oxygen, nitrogen and sulfur, which heterocyclic radical may be substituted by an alkyl radical having from 1 to 5 carbon atoms in a straight or branched chain or by an aralkyl radical, such as, for example, a benzyl radical, the aryl moiety of which is optionally substituted by one or more alkyl and alkoxy radicals each having from 1 to 5 carbon atoms in a straight or branched chain,
    ε) an amino radical of the formula

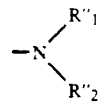

in which each of R''$_1$ and R''$_2$, which may be identical or different, represents:
  hydrogen, or alkyl or hydroxyalkyl each having from 1 to 5 carbon atoms in a straight or branched chain, or
  R''$_1$ and R''$_2$ form together with the nitrogen atom to which they are bonded a heterocycle optionally containing another hetero atom: oxygen, nitrogen or sulfur,
    ζ) a radical —OR''' in which R''' represents hydrogen, an alkyl radical having from 1 to 5 carbon atoms in a straight or branched chain or a group —COA in which: A represents an alkyl radical having from 1 to 5 carbon atoms in a straight or branched chain, or a radical

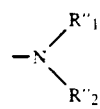

in which R''$_1$ and R''$_2$ are as defined above, and
    η) SO$_3$H and SO$_3$M in which M represents an alkali metal;
  c) an acyl radical of the formula: —COR''' in which R''' represents:
    an alkyl radical having from 1 to 10 carbon atoms in a straight or branched chain,
    an aralkyl radical, the aryl moiety of which is optionally substituted by one or more substituents selected from halogen atoms and hydroxy radicals and alkyl and alkoxy radicals each having from 1 to 5 carbon atoms in a straight or branched chain, or
    an aryl radical optionally substituted in the same manner as the aryl moiety of the aralkyl radical defined above, in c) and
  d) tosyl,
their steroisomers and also their possible addition salts with a pharmaceutically acceptable acid or base.

Of the compounds known as anti-inflammatory agents, M. Baraldi et al. (71st Int. Conf. Prostagland. Relat. Compounds, May 28, (1990), Florence, 222 sqq) describe benzoheterocyclic compounds substituted by a 3,5-di-tert.-butyl-4-hydroxyphenyl radical. A benzoheterocyclic compound cited as an example is 5,5-dioxobenzothiadiazine. Oxygenated benzoheterocycles are described in GB-A-1 250 388 and by J. Adams (J. Org. Chem., (1967), 32, 3992-3998) which related to 3',5'-di-tert.-butyl-4'-hydroxy flavanones and chalcones substituted in various manners.

The flavones forming the subject of the invention are accordingly new and have a novel application by reason of their pharmaceutical properties.

The present invention relates also to a process for the preparation of the compounds of the general formula (I), characterised in that:

A) the compound of the general formula (II):

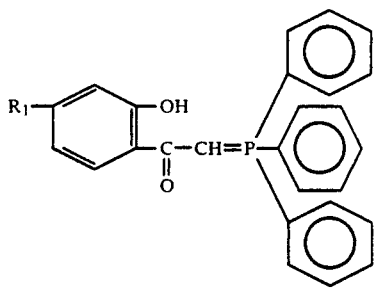

in which $R_1$ represents hydrogen or hydroxy is reacted with a halogenated compound of the general formula (III):

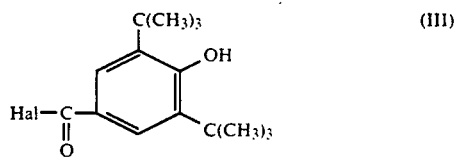

in which Hal is halogen, to yield, depending on whether $R_1$ represents a hydrogen atom or a hydroxy radical, either the compound of the formula (Ia):

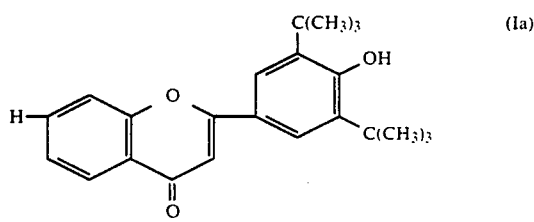

or, after alkaline treatment, the compound of the formula (Ib):

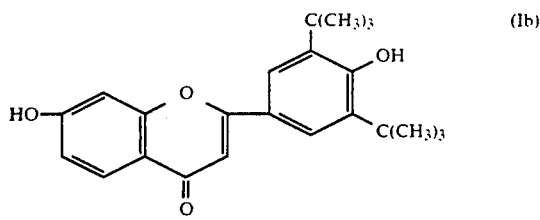

and

B) the compound (Ib) so obtained is treated with a compound of the general formula (IV):

in which $R'_A$ is as defined for $R'$, except that it cannot be a hydrogen atom, and X represents a suitable leaving group, such as, for example, a halogen atom, a tosyl radical or a sulfate radical, to yield the compounds of the general formula (Ic):

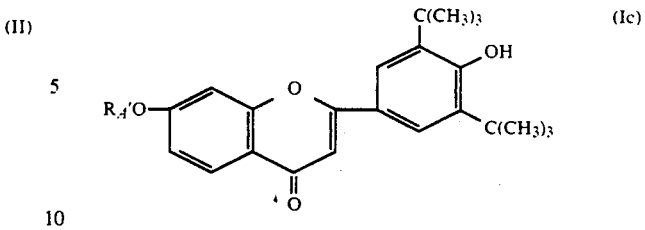

in which $R'_A$ is as defined above, all of the compounds of formulae (Ia), (Ib) and (Ic) forming all of the compounds of the general formula (I), which are purified in accordance with a customary purification technique and which are converted, where appropriate, into their addition salts with a pharmaceutically acceptable acid or base.

The reaction of the compounds (II) and (III) is carried out in an especially suitable manner by operating in a suitable solvent, such as, for example, pyridine or a mixture of toluene and pyridine, while heating under reflux for approximately three hours.

The reaction of the compounds (Ib) and (IV) is carried out in a suitable medium, such as dimethylformamide in the presence of potassium hydrogen carbonate.

The compound of formula (Ib) has also been prepared by treating with sodium hydroxide the compound of the general formula (Ic) in which $R'_A$ is limited to one acyl radical of the formula: —COR''' in which R''' represents:

an alkyl radical having from 1 to 10 carbon atoms in a straight or branched chain, an aralkyl radical, the aryl moiety of which is optionally substituted by one or more substituents selected from halogen atoms and hydroxy radicals and alkyl and alkoxy radicals each having from 1 to 5 carbon atoms in a straight or branched chain, or an aryl radical optionally substituted in the same manner as the aryl moiety of the aralkyl radical defined above.

Compounds of the general formula (Ic) in which $R'_A$ contains a terminal carboxylic acid grouping have also been prepared by hydrolysis of their corresponding esters.

The salt of this carboxylic acid has been readily prepared by simple salification with sodium hydrogen carbonate in the presence of tetrahydrofuran and water.

Compounds of the general formula (Ic) in which $R'_A$ contains a higher alkyl ester function (alkyl chain containing at least 4 carbon atoms) have also been prepared by transesterification under reflux for 5 hours in the presence of p-toluenesulfonic acid.

Another method used to prepare the compound of the general formula (Ic) in which $R'_A$ contains a sulfonic acid function is the reaction of the compound of the general formula (Ib) with 1,3-propanesultone (V):

while heating for 3 hours at approximately 110° C. in the presence of potassium hydrogen carbonate in dimethylformamide.

The new compounds of the present invention possess valuable pharmacological and therapeutic properties. In particular, it has been demonstrated in vitro that these compounds have the capacity on the one hand to protect human LDLs (Low Density Lipoproteins: lipoproteins of low density that effect the transport of cholesterol) against oxidative modifications induced by copper and by endothelial cells; and, on the other hand, to induce vascular relaxation, especially coronary vascular relaxation.

The oxidative modifications to LDLs seem at present to constitute an important mechanism in the formation and extension of atheromatous vascular lesions.

In a general manner, the compounds of the present invention can be used for protection against vascular tissue disorders related to the oxidation of biological structures. They can be used especially as a medicament in the treatment:
of dyslipidemias in order to prevent their complications, especially vascular complications,
of atherosclerosis with its various vascular, peripheral, coronary and cerebral localisations,
and also pathologies in which membrane lipid peroxidation plays an initiating and/or potentiating role, such as ischaemic cardiopathies, the reperfusion of organs, including transplanted organs, ischaemic, traumatic or degenerative pathologies of the central or peripheral nervous system, acute or chronic inflammatory diseases and auto-immune diseases.

In addition, the anti-spastic properties in respect of the large vascular trunks and the vasodilatory properties of the products of the invention have proved to be valuable in the field of coronary, cerebral and peripheral vascular pathologies both by reason of their symptomatic manifestations and by reason of the prevention of the spreading and complication of atherosclerotic vascular lesions.

The compounds of the invention can accordingly be used in vascular protection, in the arterial, microcirculatory and venovenular field, and especially for chronic, functional and organic venous insufficiency.

The invention extends also to pharmaceutical compositions containing as active ingredient at least one compound of the general formula (I) in association with one or more suitable inert non-toxic excipients.

The pharmaceutical compositions so obtained can be presented in various forms, the most advantageous being tablets, dragees, gelatin capsules, suppositories, and injectable or drinkable solutions. The mode of administration will be oral, rectal or parenteral, as appropriate.

The dosage used can be adapted in accordance with the nature and severity of the disorder, the mode of administration and also in accordance with the age and weight of the patient. As a rule, the unit dose will range from 25 mg to 1 g per day taken in one or two dosages.

The following Examples illustrate the present invention but do not limit it in any way. The starting products are known or are prepared according to customary methods of operation starting from known starting materials.

The melting points ($\Theta_f$° C.) of the compounds of the invention are determined by the micro-Kofler method and are indicated in the Table of exemplified products.

EXAMPLE 1

3′,5′-di-tert.-butyl-7,4′-dihydroxyflavone a) Preparation of 3,5-di-tert.-butyl-4-hydroxybenzoyl chloride 27 g (108.1 mmol) of 3,5-di-tert.-butyl-4-hydroxybenzoic acid are added in portions to 70 ml of ice-cooled thionyl chloride. After complete dissolution, the mixture is heated under reflux for one hour. The excess thionyl chloride is then eliminated by distillation in vacuo and the dry residue crystallises by cooling.

b) Condensation

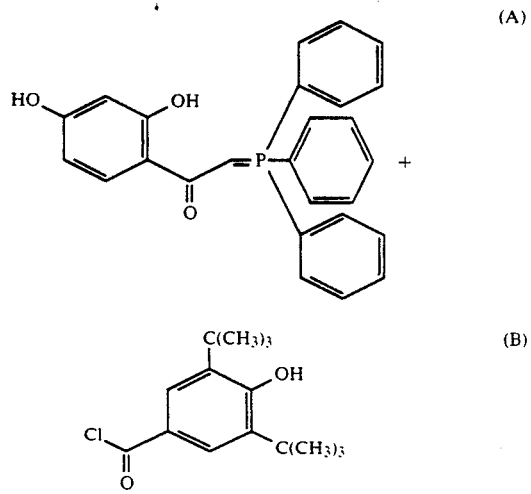

19.4 g (47 mmol) of phosphorane (A) are solubilised in 450 ml of anhydrous pyridine at 100° C. While maintaining the temperature at from 70° to 80° C., the crude acyl chloride (B), in solution in 160 ml of anhydrous toluene, is added to the pyridine solution over a period of approximately 10 minutes.

The reaction is maintained at the same temperature for three hours, with stirring, and is then left to stand overnight at ambient temperature.

The reaction mixture is filtered, poured onto ice and extracted with methylene chloride.

After washing and then drying over sodium sulfate, the organic phase is evaporated under reduced pressure.

The dry residue is dissolved in 500 ml of a 0.5N methanolic sodium hydroxide solution. The whole is left overnight at ambient temperature under a nitrogen atmosphere.

The reaction mixture is then diluted with water and extracted several times with cyclohexane.

The aqueous phase is then adjusted to a pH of 6 by the addition of hydrochloric acid and then extracted with methylene chloride. After drying over sodium sulfate, the organic phase is filtered and evaporated to yield 4.96 g of the expected product in the form of a dry crystalline residue.

Yield: 29 %.

EXAMPLE 2

3′,5′-di-tert.-butyl-7-n-hexyloxy-4′-hydroxyflavone 0.183 g (0.5 mmol) of the compound of Example 1 and 0.25 g (2.5 mmol) of potassium hydrogen carbonate are stirred for a few moments in 10 ml of dimethylformamide at 110° C. under nitrogen until they have completely dissolved. 0.7 ml (5 mmol) of [1-bromo-n-hexane] are then added and the reaction is continued under the same conditions for two hours.

The reaction mixture is then taken up in water and extracted with diethyl ether.

After customary treatment and crystallisation of the dry residue from a mixture of methylene chloride and methanol, 0.133 g of the expected product is obtained.
Yield: 60 %.

EXAMPLE 3

3',5'-di-tert.-butyl-4'-hydroxy-7-(4"'-morpholinylethoxy)flavone

This product is obtained in accordance with the same procedure as that described in Example 2 by replacing the [1-bromo-n-hexane] with 2-(4'-morpholinyl)-1-chloroethane.

EXAMPLE 4

7-p-chlorobenzyloxy-3',5'-di-tert.-butyl-4'-hydroxyflavone

Procedure identical to that of Example 3, using p-chlorobenzyl chloride.

EXAMPLE 5

3',5'-di-tert.-butyl-4'-hydroxy-7-(2"-piperidino-2"-oxoethoxy)flavone

Procedure identical to that of Example 3, using 1-piperidino-1-oxo-2-chloroethane.

EXAMPLE 6

3',5'-di-tert.-butyl-4'-hydroxy-7-[2"-(N-benzyl-piperazino)-2"-oxo-ethoxy]flavone Procedure identical to that of Example 3, using 1-(N-benzylpiperazino)-1-oxo-2-chloroethane.

EXAMPLE 7

3',5'-di-tert.-butyl-4'-hydroxy-7-(N,N-diethylacetamicoxy) flavone

Procedure identical to that of Example 3, using (N,N-diethyl)chloroacetamide.
Yield: 59%.

EXAMPLE 8

3',5'-di-tert.-butyl-4'-hydroxy-7-(2"'-quinolylmethoxy)-flavone

Procedure identical to that of Example 3, using chloro(2-quinolyl)methane.

EXAMPLE 9

3',5'-di-tert.-butyl-4'-hydroxy-7-[2-(N,N-dimethylamino) ethoxy]flavone

Procedure identical to that of Example 3, using 2-(N,N-dimethylamino)-1-chloroethane.

EXAMPLE 10

3',5'-di-tert.-butyl-4'-hydroxy-7-[3"-(N,N-dimethylamino) propoxy]flavone

Procedure identical to that of Example 3, using 3-(N,N-dimethylamino)-1-chloropropane.

EXAMPLE 11

Ethyl 5-[7-(3',5'-di-tert.-butyl-4'-hydroxy)flavonyl]oxyvalerate

Procedure identical to that of Example 3, using ethyl 1-bromovalerate.

EXAMPLE 12

3-[7-(3',5'-di-tert.-butyl-4'-hydroxy)flavonyl]oxypropanesulfonic acid

Same procedure as that described in Example 3, replacing the halogenated compound with 1,3-propanesultone.

EXAMPLE 13

3',5'-di-tert.-butyl-4'-hydroxy-7-(2-hydroxyethoxy)flavone

Same procedure as that described in Example 3, using 2-chloro-1-hydroxyethane.

EXAMPLE 14

3',5'-di-tert.-butyl-4'-hydroxyflavone

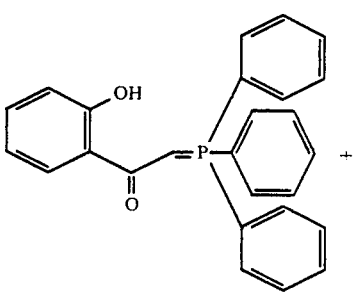

(A')

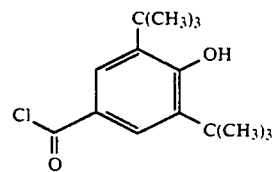

(B)

1.402 g (1.5 mmol) of acyl chloride (B) are added to 100 ml of a mixture of toluene and pyridine (95:5) and 0.806 g (1 mmol) of phosphorane (A'). The whole is heated under reflux for 3 hours.

The reaction mixture is filtered, poured onto ice and extracted with methylene chloride.

After washing and drying over sodium sulfate, the organic phase is evaporated under reduced pressure.

The expected product is then crystallised from methanol.

EXAMPLE 15

Ethyl 2-[7-(3',5'-di-tert.-butyl-4'-hydroxy)flavonyl]oxy-2,2-dimethyl acetate

Same procedure as that described in Example 3, using ethyl 2-bromoisobutyrate.

EXAMPLE 16

Ethyl 2-(3',5'-di-tert.-butyl-4'-hydroxy)flavonyl]oxyacetate

Same procedure as that described in Example 3, using ethyl 2-chloroacetate.
Yield: 66%.

EXAMPLE 17

2-[7-(3',5'-di-tert.-butyl-4'-hydroxy)flavonyl]oxyacetic acid 0.452 g (1 mmol) of the product obtained in Example 16 is dissolved in 20 ml of tetrahydrofuran.

60 ml of aqueous 1N sodium hydroxide solution are added and the reaction is maintained at ambient temperature for six hours with stirring and under a nitrogen atmosphere.

The reaction mixture is then diluted with water, acidified with hydrochloric acid to pH 2 and then extracted with methylene chloride.

Customary treatment of the organic phase yields a dry residue in the form of a microcrystalline power.
Yield: 95%.

EXAMPLE 18

Sodium 2-[7-(3',5'-di-tert.-butyl-4'-hydroxy)flavonyl]oxyacetate 0.424 g (1 mmol) of the product obtained in Example 17 is dissolved in a 3/5:2/5 tetrahydrofuran/water mixture. 0.084 g (1 mmol) of sodium hydrogen carbonate is added to yield the expected product after customary treatment and evaporation to dryness.

EXAMPLE 19

Pentyl 2-[7-(3',5'-di-tert.-butyl-4'-hydroxy)flavonyl]oxtyacetate 0.271 g (0.6 mmol) of the product obtained in Example 16 and 0.030 g of p-toluenesulfonic acid are dissolved in 20 ml of n-pentanol. The mixture is stirred for 4 hours at 125° C.

The reaction mixture is then diluted with water and extracted with methylene chloride. After customary treatment of the organic phase, the dry residue obtained yields the expected product by crystallisation from a mixture of methylene chloride and methanol.
Yield: 73%.

EXAMPLE 20

3',5'-di-tert.-butyl-4'-hydroxy-7-(3'',5''-di-tert.-butyl-4''-hydroxy)benzoyloxyflavone 0.335 g (1.25 mmol) of crude 3,5-di-tert.-butyl-4-hydroxybenzoyl chloride in solution in 2 ml of toluene is added to 0.366 g (1 mmol) of the product of Example 1 dissolved in 5 ml of pyridine. After 24 hours at ambient temperature, the reaction mixture is taken up in water and then extracted with methylene chloride. The organic phase is washed and then dried over sodium sulphate and evaporated to dryness. After recrystallisation from methanol, 0.420 g of the expected product is obtained.

This compound was also prepared directly by condensing the phosphorane (A) with excess acyl chloride (B).

EXAMPLE 21

3',5'-di-tert.-butyl-4'-hydroxy-7-(2,3-dihydroxy-n-propoxy) flavone

Same procedure as that described in Example 3, the terminal alcohol of the reagent being protected by a tosyl grouping.

TABLE OF EXEMPLIFIED PRODUCTS

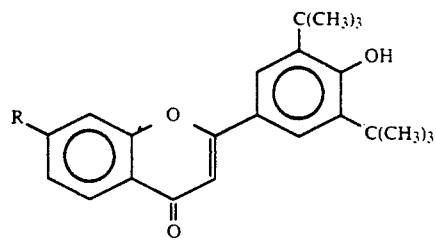

| Examples no | R | $\theta_f$ (°C.) |
|---|---|---|
| 1 | —OH | 298–300 |
| 2 | —O—$C_6H_{13}$ | 133–135 |
| 3 | —O—$(CH_2)_2$—N(morpholino) | 175–176 |
| 4 | —$OCH_2$—$C_6H_4$—Cl | 190–191 |
| 5 | —$OCH_2CON$(piperidino) | 215–216 |
| 6 | —$OCH_2$—CON(piperazino)N—$CH_2$—Ph | 167–169 |
| 7 | —$OCH_2CON(Et)_2$ | 180–182 |
| 8 | —O—$CH_2$-quinolinyl | 213–215 |
| 9 | —$OCH_2CH_2$—N(Me)(Me) | 136–137 |
| 10 | —O—$(CH_2)_3$—N(Me)(Me) | 183–185 |
| 11 | —O—$(CH_2)_4$—$CO_2Et$ | 131–132 |
| 12 | —O—$(CH_2)_3SO_3H$ | 290–292 |
| 13 | —O—$(CH_2)_2OH$ | 230–231 |
| 14 | —H | 195–197 |
| 15 | —O—$C(CH_3)_2CO_2Et$ | 167–169 |
| 16 | —$OCH_2CO_2Et$ | 172–174 |
| 17 | —$OCH_2CO_2H$ | Amorphous |
| 18 | —$OCH_2CO_2Na$ | Amorphous |
| 19 | —$OCH_2CO_2C_5H_{11}$ | 175–177 |

-continued
TABLE OF EXEMPLIFIED PRODUCTS

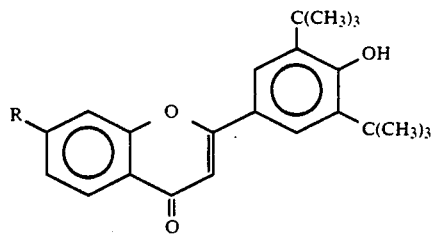

| Examples no | R | θ_f (°C.) |
|---|---|---|
| 20 | —OCO—⟨C(CH₃)₃, OH, C(CH₃)₃⟩ | 268–270 |
| 21 | —OCH₂—CH(OH)—CH₂—OH | 190–191 |

PHARMACOLOGICAL STUDY

The action of the compounds of the present invention was demonstrated on the one hand on human and animal LDLs and, on the other hand, on isolated vessels.

The inhibitory activity of the compounds with respect to the oxidative modification of LDLs, induced by copper sulphate (Example 21) and by endothelial cells of the rabbit aorta (Example 22) was demonstrated in vitro. This activity was compared with that of probucol and vitamin E taken as reference products.

The vasorelaxant activity was demonstrated on coronary arteries caused to contract by F2α prostaglandin (PGF2α) (Example 23).

EXAMPLE 22

Modification of LDLs by copper sulphate

Human LDLs are incubated for 24 hours in the presence of copper sulfate (5 μM) and in the absence or in the presence of the compounds tested (from 0.1 μM to 100 μM).

After incubation, the peroxidation of the LDLs is evaluated by electrophoresis on agar gel and by the formation of one of the products of lipid peroxidation: malonic dialdehyde (MDA) (cf. Parthasarathy S. et al., J. Clin. Invest., 77, (1986), 641–644).

The activity of the compounds tested is evaluated by calculating the concentrations that reduce by 50% (IC$_{50}$) the production of MDA compared with the control experiments in the absence of a product of the invention.

The results of this test of inhibition of oxidation of LDLs by copper sulfate are listed in the following Table.

| COMPOUNDS | IC$_{50}$ (μM) |
|---|---|
| Example 1 | 1 |
| Example 2 | 5 |
| Example 3 | 0.8 |
| Example 4 | 7 |
| Example 5 | 3 |
| Example 6 | 3 |
| Example 7 | 3 |
| Example 14 | 3 |
| Example 15 | 3 |
| Example 16 | 3 |
| Example 17 | 3 |
| Example 18 | 5 |
| Example 20 | 30 |
| PROBUCOL | 3 |
| VITAMIN E | >100 |

EXAMPLE 23

Modification of LDLs by endothelial cells

Human LDLs are incubated for 24 hours in the presence of endothelial cells of the rabbit aorta (RECL B4 line, provenance: Pr. Steinberg, U.S.A.) and in the absence or in the presence of the tested compounds (from 0.1 to 100 μM).

After incubation, the peroxidation of the LDLs is evaluated as in Example 21 by electrophoresis on agar gel and by the formation of MDA (cf. Steinbrecher, U.P. et al., Proc. Natl. Acad. Sci, USA, 81, (1984), 3883–3887). The activity of the compounds tested is evaluated by calculating the concentrations that reduce by 50% (IC$_{50}$) the production of MDA compared with the control experiments in the absence of a product of the invention.

The results of this test of inhibition of oxidation of LDLs by endothelial cells are grouped below:

| COMPOUNDS | IC$_{50}$ (μM) |
|---|---|
| Example 14 | 2.5 |
| Example 15 | 0.5 |
| Example 16 | 0.8 |
| Example 17 | 0.5 |
| Example 20 | 0.7 |
| PROBUCOL | 4 |
| VITAMIN E | 4 |

EXAMPLE 24

Study of the compounds of the invention on isolated vessels

Yucatan miniature pigs (Ch. River) are anaesthetised with pentobarbitone. The circumflex branch of the left coronary artery is removed and proximal rings of approximately 4 mm are prepared. The organs are placed in a temperature-controlled 20 ml bath containing a physiological solution having the composition:
NaCl: 118 mmol
KCl: 4.7 mmol
KH$_2$PO$_4$: 1.2 mmol
MgSO$_4$: 1.2 mmol
CaCl$_2$: 2.5 mmol
NaHCO$_3$: 20 mmol
Glucose: 11 mmol
maintained at 37° C., pH=7.4 and with 95 % oxygen and 5% carbon dioxide.

The initial tension is established progressively up to 6 g. After a stabilisation period of 60 minutes, the rings are caused to contract by PGF2α (4 μM) in the presence of indomethacin (10 μM). As soon as this concentration has stabilised, the products of the present invention are tested by adding cumulative concentrations of the product of Example 17 and probucol every 15 minutes in comparison with the control experiments with the solvent used (dimethyl sulfoxide: DMSO).

The following Table shows the evolution of the tensions measured as a percentage of the maximum tension observed under PGF2α.

| Products tested | Concentrations (μM) | | | | |
|---|---|---|---|---|---|
| | 0.1 | 0.3 | 1 | 3 | 10 |
| Example 16 | 95.4 ± 2.1 | 85.0 ± 5.4 | 74.1 ± 5.7 | 37.3 ± 11.6 | 20.2 ± 10.9 |
| DMSO | 87.9 ± 7.3 | — | 80.7 ± 10.5 | — | 72.0 ± 12.1 |
| PROBUCOL | 93.3 ± 3.3 | 85.6 ± 4.7 | 77.3 ± 6.1 | 66.01 ± 7.9 | 49.2 ± 11.6 |

The product of Example 16, unlike probucol, brings about a concentration-dependent vascular relaxation enabling the calculation of an IC$_{50}$ having a value of approximately 2.6 μM.

The activity of several compounds of the invention is superior to that of probucol as regards the modifications induced by copper sulfate and by endothelial cells.

The compounds of the invention are also more powerful than vitamin E in these two tests.

All of the reported results demonstrate that the compounds of the invention have, at similar concentrations, a two-fold activity: on the one hand an anti-oxidant activity protecting especially LDLs against pathogenic oxidative modifications and, on the other hand, an anti-vasoconstrictive activity, especially on the coronary arteries.

This novel profile differs especially from that of probucol and the other anti-oxidants described and demonstrates the great therapeutic value of the products of the invention.

We claim:

1. A method for treating an animal or human living body afflicted with a disease, requiring an antioxidant and anti-vaso constrictor, resulting from a vascular tissue disorder related to the oxidation of biological structures, comprising the step of administering to the said body an effective amount of a compound selected from those of formula (I):

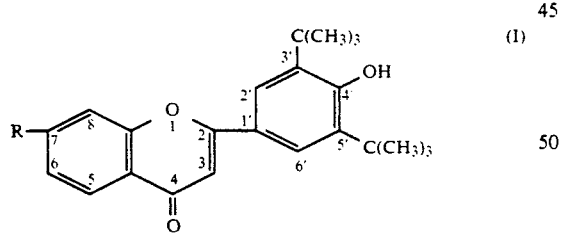

in which:
R represents:
hydrogen or
a radical OR' in which R' represents:
a) hydrogen
b) an alkyl radical containing 1 to 10 carbon atoms inclusive in a straight or branched chain optionally substituted by one or more substituents selected from the group consisting of:
α) phenyl and monocyclic or bicyclic aromatic heterocyclic radicals, all optionally substituted by one or more substituents selected from halogen atoms and trifluoromethyl and hydroxy radicals and alkyl and alkoxy radicals each having 1 to 5 carbon atoms inclusive in a straight or branched chain, β) carboxy, γ) alkoxycarbonyl in which the alkoxy group contains 1 to 5 carbon atoms inclusive in a straight or branched chain, δ) aminocarbonyl of the formula:

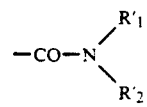

in which each of R'$_1$ and R'$_2$, which may be identical or different, represent: hydrogen, or an alkyl radical having 1 to 5 carbon atoms inclusive in a straight or branched chain, or R'$_1$ and R'$_2$ form together with the nitrogen atom to which they are bonded a heterocyclic radical optionally containing a second hetero atom selected from oxygen, nitrogen and sulfur, which heterocyclic radical may be substituted by an alkyl radical having 1 to 5 carbon atoms inclusive in a straight or branched chain or by an aralkyl radical, the aryl moiety of which is optionally substituted by one or more alkyl and alkoxy radicals each having 1 to 5 carbon atoms inclusive in a straight or branched chain, ε) an amino radical of the formula

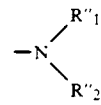

in which each of R''$_1$ and R''$_2$, which may be identical or different, represents:
hydrogen, or an alkyl or hydroxyalkyl radical each having 1 to 5 carbon atoms inclusive in a straight or branched chain, or
R''$_1$ and R''$_2$ form together with the nitrogen atom to which they are bonded a heterocycle optionally containing another hetero atom selected from oxygen, nitrogen, and sulfur, ζ) a radical —OR'' in which R'' represents hydrogen, an alkyl radical having 1 to 5 carbon atoms inclusive in a straight or branched chain or a group —COA in which: A represents an alkyl radical having 1 to 5 carbon atoms inclusive in a straight or branched chain, or a radical

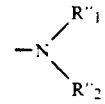

in which R''$_1$ and R''$_2$ are as defined above, and

η) —SO$_3$H or —SO$_3$M in which M represents an alkali metal;

c) an acyl radical of the formula: —COR''' in which R''' represents:
   an alkyl radical having 1 to 10 carbon atoms inclusive in a straight or branched chain,
   an aralkyl radical, the aryl moiety of which is optionally substituted by one or more substituents selected from halogen atoms and hydroxy radicals and alkyl and alkoxy radicals each having 1 to 5 carbon atoms inclusive in a straight or branched chain, or
   an aryl radical optionally substituted in the same manner as the aryl moiety of the aralkyl radical defined above, in c) and
d) tosyl, their stereoisomers and also their possible addition salts with a pharmaceutically-acceptable acid or base.

2. Method of claim 1 wherein the compound is 3',5'-di-tert.-butyl-7,4'-dihydroxyflavone.

3. Method of claim 1 wherein the compound is 3',5'-di-tert.-butyl-4'-7-n-hexyloxyflavone.

4. Method of claim 1 wherein the compound is 3',5'-di-tert.-butyl-4'-7-(4'''-morpholinylethoxy) flavone.

5. Method of claim 1 wherein the compound is 3',5'-di-tert.-butyl-4'-hydroxy-7-p-chlorobenzyloxy flavone.

6. Method of claim 1 wherein the compound is 3',5'-di-tert.-butyl-4'-hydroxy-7-(2'''-piperidino-2'''-oxoethoxy)flavone.

7. Method of claim 1 wherein the compound is 3',5'-di-tert.-butyl-4'-hydroxy-7-[2'''-(N-benzylpiperazino)-2'''-oxo-ethoxy]flavone.

8. Method of claim 1 wherein the compound is 3',5'-di-tert.-butyl-4'-hydroxy-7-(N,N-diethylacetamidoxy) flavone.

9. Method of claim 1 wherein the compound is 3',5'-di-tert.-butyl-4'-hydroxy-7-(2'''-quinolylmethoxy) flavone.

10. Method of claim 1 wherein the compound is 3',5'-di-tert.-butyl-4'-hydroxy-7-[2-(N,N-dimethylamino)ethoxy]flavone.

11. Method of claim 1 wherein the compound is 3',5'-di-tert.-butyl-4'-hydroxy-7-[3'''-(N,N-dimethylamino)propoxy]flavone.

12. Method of claim 1 wherein the compound is Ethyl 5-[7-(3',5'-di-tert.-butyl-4'-hydroxy)flavone] oxyvalerate.

13. Method of claim 1 wherein the compound is 3-[7-(3',5'-di-tert.-butyl-4'-hydroxy)flavone] oxypropanesulfonic acid.

14. Method of claim 1 wherein the compound is 3',5'-di-tert.-butyl-4'-hydroxy-7-(2-hydroxyethoxy) flavone.

15. Method of claim 1 wherein the compound is 3',5'-di-tert.-butyl-4'-hydroxyflavone.

16. Method of claim 1 wherein the compound is Ethyl 2-[7-(3',5'-di-tert.-butyl-4'-hydroxy)flavone]oxy-2,2-dimethyl acetate.

17. Method of claim 1 wherein the compound is Ethyl 2-[7-(3',5'-di-tert.-butyl-4'-hydroxy)flavone] oxyacetate.

18. Method of claim 1 wherein the compound is 2-[7-(3',5'-di-tert.-butyl-4'-hydroxy)flavone]oxyacetic acid.

19. Method of claim 1 wherein the compound is Sodium 2-[7-(3',5'-di-tert.-butyl-4'-hydroxy)flavone] oxyacetate.

20. Method of claim 1 wherein the compound is Pentyl 2-[7-(3',5'-di-tert.-butyl-4'-hydroxy)flavone] oxyacetate.

21. Method of claim 1 wherein the compound is 3',5'-di-tert.-butyl-4'-hydroxy-7-(3'',5''-di-tert.-butyl-4''-hydroxybenzoyloxy)flavone.

* * * * *

UNITED STATES PATENT AND TRADEMARK OFFICE
CERTIFICATE OF CORRECTION

PATENT NO. : 5,280,024
DATED : Jan. 18, 1994
INVENTOR(S) : Yves Rolland, Guy Lewin, Jean-Paul Vilane, Albert Lenaers, Catherine Thollon It is certified that error appears in the above-indentified patent and that said Letters Patent is hereby corrected as shown below:

```
Title Page, under "United States Patent [19]"; "Bolland et al"
      should read -- Rolland et al. --.
Title Page, Column 1, [75] Inventors: line 1; "Bolland"
      should read -- Rolland --.
Title Page, Column 1, [75] Inventors: line 3; "Lenaers
      Albert" should read -- Albert Lenaers --.
Column 2, line 59; "related" should read -- relate --.
Column 7, approximately line 38; "thylacetamicoxy)" should read
      -- thylacetamidoxy) --.
Column 9, line 31; oxtyace-" should read --oxyace- --.
Column 15, line 22; "4'-7-n-" should read -- 4'-hydroxy-7-n---.
Column 15, line 24; "4'-7-" should read -- 4'-hydroxy-7- --.
Column 16, line 11, 14, 21, 24, 27, 29, and 32;
      "flavone]"should read --flavonyl] --.
```

Signed and Sealed this

Twentieth Day of September, 1994

Attest:

BRUCE LEHMAN

Attesting Officer

Commissioner of Patents and Trademarks